United States Patent [19]

Craven

[11] 4,170,126
[45] Oct. 9, 1979

[54] THERMAL CONDUCTIVITY CELL WITH THICK FILM SEAL

[75] Inventor: John S. Craven, West Grove, Pa.

[73] Assignee: Hewlett-Packard Company, Palo Alto, Calif.

[21] Appl. No.: 885,824

[22] Filed: Mar. 13, 1978

[51] Int. Cl.² ............................................ G01N 31/00
[52] U.S. Cl. ................................ 73/27 A; 277/DIG. 6
[58] Field of Search .................. 73/15 A, 27 A, 27 R, 73/25, 26; 106/47 R, 53; 277/DIG. 6

[56] References Cited

U.S. PATENT DOCUMENTS 3,154,503  10/1964  Rao et al. ........................... 106/53 X
3,888,110  6/1975  Clark .................................... 73/27 R Primary Examiner—Jerry W. Myracle
Attorney, Agent, or Firm—Donald N. Timbie

[57] ABSTRACT

A thermal conductivity cell is provided that is made of cast wafers of ceramic material having a groove in one or both planar abutting surfaces. A filament is mounted in the groove by attachment to the ends of electrical conductors that extend through one of the wafers in sealed relationship. Passageways extend between points in the groove and an exterior surface of the cell. Gaskets are formed on the exterior surface around the openings where the passageways emerge. The gaskets are formed by silk screening and firing one or more layers of thick film conductor paste onto the surface of a layer of thick film conductor paste and at least one superimposed layer of gold and binder.

12 Claims, 5 Drawing Figures

THERMAL CONDUCTIVITY CELL WITH THICK FILM SEAL

BACKGROUND OF THE INVENTION

A thermal conductivity cell used in a thermal conductivity detector is generally comprised of an electrically heated filament mounted in a cavity through which the carrier gas and sample gas eluting from a gas chromatograph column may be passed. As the concentration of the sample gas in the carrier gas changes, it varies the rate at which heat flows from the filament to the walls of the cavity and, consequently, the amount of electrical power required to keep the filament at a constant resistance or temperature. Accordingly, a measurement of this power can be used as an indication of the concentration of sample gas in the carrier gas flowing through the cavity.

In a U.S. patent application, Ser. No. 730,559, entitled "Modulated Fluid Detector", and filed on Oct. 7, 1976, in the name of David E. Clouser and myself, a thermal conductivity cell is disclosed that is comprised of two wafers having a groove in one or both abutting planar surfaces. A filament is mounted in an intermediate portion of the groove, and electrical conductors that are connected to respective ends of the filament are passed in sealed relationship through one of the wafers to points outside the cell. A number of passageways are provided in the other wafer for communicating from different points outside of the cell to predetermined points in the groove. Connections from these passageways to various points in the chromatograph are provided by bonding metal tubing in communicating relationship with the passageways.

As it is necessary to replace the cell from time to time because of filament failure or other defects, it is desirable that its initial cost be low and that its structure be such that it can be easily replaced in the field without special equipment. Making the wafers of the cell from ceramic material instead of metal would make its initial cost very low, but presently known techniques for bonding the metal tubes to the passageways in a ceramic wafer, while satisfactory for use in the factory, are so difficult to use in the field that it would be easier and more economical to throw away the expensive metal tubes along with the defective cell.

BRIEF DISCUSSION OF THE INVENTION

These problems are overcome by a thermal conductivity cell constructed in accordance with this invention. The cell is comprised of two ceramic wafers having planar abutting surfaces. A groove is formed in at least one of the surfaces and a filament is mounted therein by attachment to electrical conductors that pass through one of the wafers. Passageways communicating between required points in the groove and the exterior of the cell can be formed in one of the planar surfaces, but it is preferable that they extend from the groove through one or both of the wafers to the exterior of the cell. Wherever a passageway emerges from the exterior surface of the cell, it is surrounded by a gasket made from thick film conductor paste. A pair of metal plates are placed on opposite sides of the cell, one of the plates having openings through which the electrical conductors can pass and the other plate having holes passing therethrough in registration with the openings in the cell where the passageways emerge therefrom. The plates are pressed together by bolts passing through them so as to squeeze the gaskets and provide sealed communication between passageways in the cell and the holes in the metal plate. This forms a detector assembly. Metal tubes for connecting the detector assembly to points in the chromatograph are bonded to the holes in the metal plate. When it is necessary to replace a cell, the bolts are removed, the defective cell is removed, and a new cell is put in its place. The gaskets on the new cell are compressed so as to form a seal by suitably tightening the bolts.

THE DRAWINGS

Figure 1:
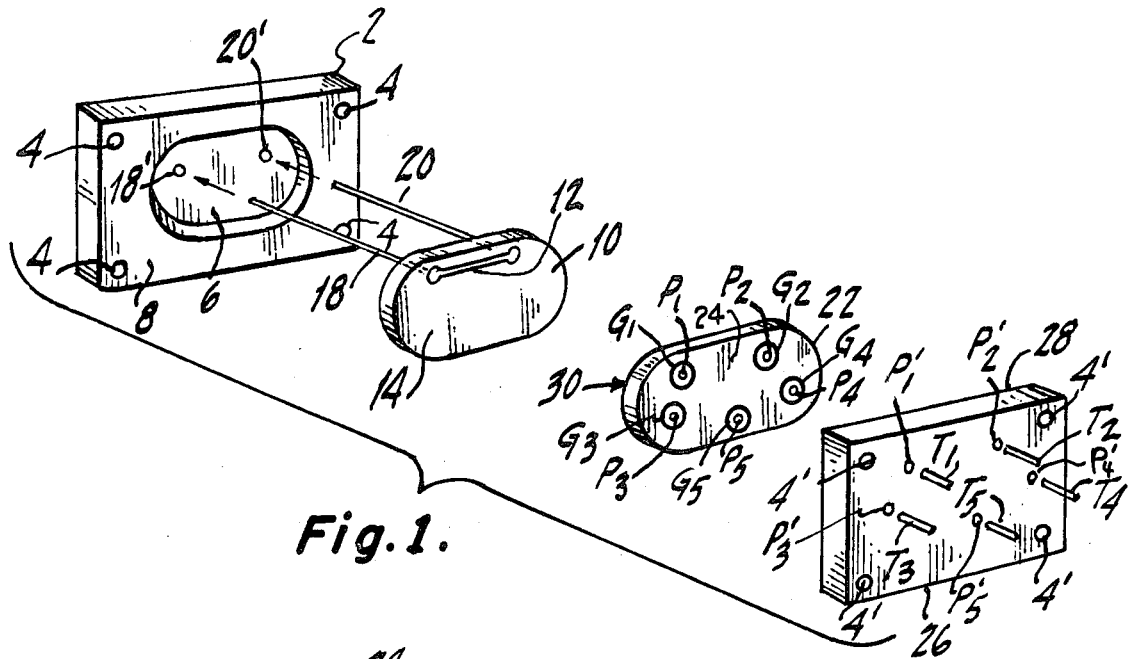
FIG. 1 is an exploded view of a thermal conductivity detector assembly of this invention viewed from a first direction.

Referring to FIG. 1, there is shown a rectangular metal plate 2 having holes 4 extending through at the corners thereof and a depression 6 in a planar surface 8. A ceramic wafer 10 is shaped so as to fit closely in the depression 6. A longitudinal filament 12 is mounted by attachment to stiff electrical conductors 18 and 20 that pass from the ends of the filament 12 through the wafer 10 in sealed relationship therewith. The conductors 18 and 20 are aligned with holes 18' and 20' in the depression 6 in the metal plate 2.

One end of each of five passageways $P_1$, $P_2$, $P_3$, $P_4$ and $P_5$ that extend completely through a ceramic wafer 22 are shown in a surface 24 thereof. Gaskets $G_1$, $G_2$, $G_3$, $G_4$ and $G_5$ are shown on the surface 24, respectively surrounding the openings where the passageways $P_1$, $P_2$, $P_3$, $P_4$ and $P_5$ emerge. A second metal plate 26 is provided with threaded holes 4' in each corner thereof that are in alignment with the holes 4 in the metal plate 2 so that the assembly can be drawn together by passing bolts through the aligned holes and tightening them. The metal plate 26 has passageways $P_1'$, $P_2'$, $P_3'$, $P_4'$ and $P_5'$ extending therethrough that are respectively in registration with the passageways $P_1$, $P_2$, $P_3$, $P_4$ and $P_5$ in the wafer 22. The inside surface 28 that is not seen in FIG. 1 is such that it makes contact with all of the gaskets $G_1$, $G_2$, $G_3$, $G_4$ and $G_5$. Raised islands could perform this function, but the simplest way to achieve this result is to make the surface 28 planar. The surface 28 must be sufficiently hard to withstand the compressive stress exerted by the gaskets without permanent deformation. Metal tubes $T_1$, $T_2$, $T_3$, $T_4$ and $T_5$ are normally respectively connected to the passageways $P_1'$, $P_2'$, $P_3'$, $P_4'$ and $P_5'$, but are shown unattached in order that the ends of the passageways may be shown.

The ceramic wafers 10 and 22 are bonded together so as to form a cell. The cell can be inserted between the metal plates by simply inserting the conductors 18 and 20 through the holes 18' and 20' in the metal plate 2 and nesting the wafer 10 in the depression 6. The plate 26 is then held against the surface 24 of the ceramic wafer 22 with the passageways $P_1'$, $P_2'$, $P_3'$, $P_4'$ and $P_5'$ respectively in registration with the passageways $P_1$, $P_2$, $P_3$, $P_4$ and $P_5$. The alignment can be easily achieved by use of alignment parts not shown. Bolts are inserted through each of the aligned pairs of holes 4 and 4' in the corners of the plates 2 and 26, and the assembly is squeezed together by tightening them.

Figure 2:
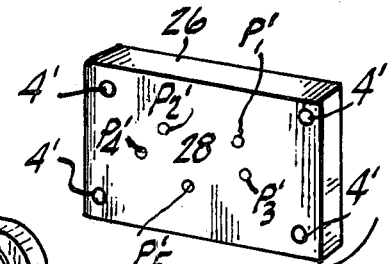
FIG. 2 is an exploded view of a thermal conductivity detector assembly of this invention viewed from a second direction.

In FIG. 2, components corresponding to those in FIG. 1 are indicated by the same numbers or letters. In this view, the inner surface 30 of the ceramic wafer 22 is seen to have a groove 32 in the form of a racetrack. The inner ends of the passageways $P_1$, $P_2$, $P_3$, $P_4$ and $P_5$ can be seen in communication with the groove 32.

Figure 3:
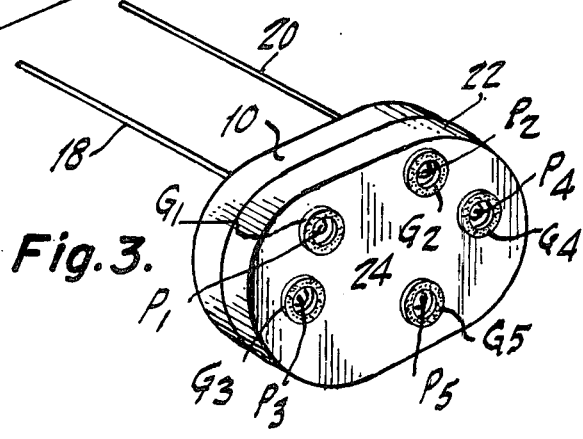
FIG. 3 is an exterior view of the ceramic cell.

FIG. 3 is an external view of a ceramic cell showing the gaskets $G_1$, $G_2$, $G_3$, $G_4$ and $G_5$ on the surface 24 around each of the passageways $P_1$, $P_2$, $P_3$, $P_4$ and $P_5$, respectively. The wafers 10 and 22 can be permanently bonded together in any suitable manner.

Figure 4:
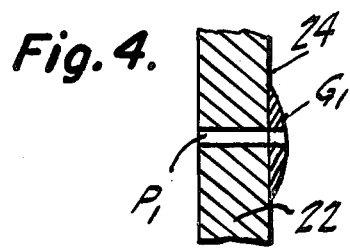
FIG. 4 is a cross-section of one of the passageways in one of the ceramic wafers of a ceramic cell in which the gasket is formed from one layer of thick film conductor paste.

FIG. 4 is a section taken through the axis of a passageway, such as $P_1$, in the ceramic wafer 22. In this particular illustration, the gasket $G_1$ is formed on the surface 24 of the wafer 22 by silk screening and firing a single layer of thick film conductor paste but, in order to obtain the desired thickness, it will be understood that a number of layers may be used. The paste is generally comprised of various percentages of gold, silver, copper and other metals, glass frit, copper or other metal oxides, and binders. A preferred paste for the purpose of this invention is a mixture of gold, less than 10% by weight of glass frit, and an organic binder.

Figure 5:
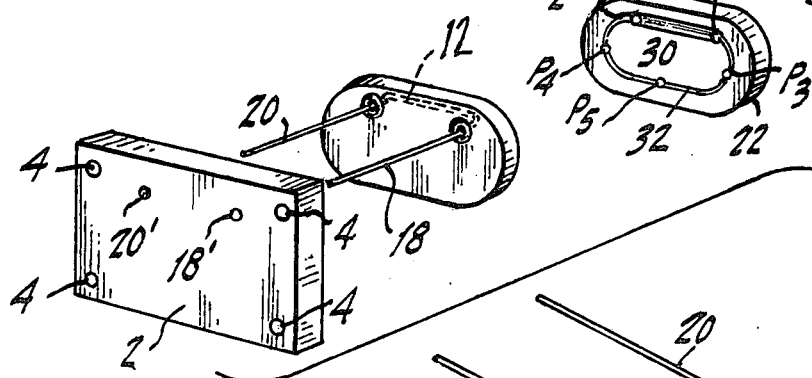
FIG. 5 is a cross-section of one of the passageways in one of the ceramic wafers of a ceramic cell in which the gasket is formed with several layers of material.
Figure 5:
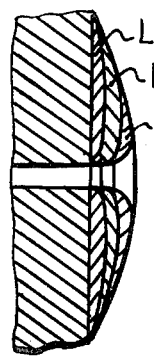

Whereas a gasket can be formed from layers of a thick film conductor paste, it has been found that the optimum configuration is comprised of a first layer $L_1$ of paste consisting of gold, glass frit and binder to provide adhesion to the ceramic surface, followed by additional layers $L_2$ and $L_3$ of paste consisting of gold and binder to provide better compressability, as illustrated in FIG. 5.

I claim:

1. A thermal conductivity cell comprising
first and second ceramic wafers having exterior surfaces and abutting and interfitting interior surfaces,
means defining a groove in at least one of said interior surfaces,
means mounting a filament in said groove,
means for making electrical connection between the ends of the filament and points outside the cell, said means being in sealed relationship with the cell,
means defining passageways communicating between points exterior to said cell and said groove, and
rings of gasket material deposited on the external surface of said cell surrounding the areas where each said passageway emerges therefrom.

2. A thermal conductivity cell as set forth in claim 1 wherein said gaskets are formed from thick film conductor paste.

3. A thermal conductivity cell as set forth in claim 2 wherein said thick film conductor paste is comprised of a mixture of particles of gold and particles of glass.

4. A thermal conductivity cell as set forth in claim 3 wherein said glass particles are less than ten percent by weight of the mixture.

5. A thermal conductivity cell as set forth in claim 3 wherein a layer of gold is formed onto the side of said gasket remote from said external surface.

6. In combination,
a thermal conductivity cell as set forth in claim 1,
a metal plate, said metal plate having means defining passageways therein emerging from a surface thereof at such points that said passageways respectively communicate with the passageways emerging from said cell, said surface of said metal plate being so shaped as to be in contact with said gaskets, and
means for pressing and holding said cell and said metal plate together so as to compress said gaskets.

7. A thermal conductivity cell as set forth in claim 6 wherein said gaskets are formed from thick film conductor paste.

8. A thermal conductivity cell comprising
first and second ceramic wafers, each having parallel planar interior and exterior surfaces,
means defining a groove in at least one of said interior surfaces,
electrical conductors extending through said first wafer and having ends extending into said groove,
a filament mounted between said ends of said conductors,
means defining passageways respectively communicating between means defining openings in the exterior surface of said second wafer and points in said groove,
a first metal plate,
means defining a pair of holes extending through said first metal plate, said first ceramic wafer being mounted with said conductors extending through said holes,
gaskets formed from thick film conductor paste bonded to the exterior surface of said second wafer,
a second metal plate having an exterior surface and a planar interior surface, said interior surface being in contact with the gaskets on said exterior surface of said second wafer,
means defining openings in said interior surface of said second metal plate, said openings being located in registration with said openings in said exterior surface of said second wafer,
means defining openings in said exterior surface of said second plate, and
means defining passageways respectively communicating between said latter openings and said openings in said interior surface of said second plate.

9. A body of ceramic material having means defining at least one opening in a surface thereof, and
a gasket comprised of a mixture of particles of gold and particles of glass mounted on said surface around said opening.

10. A body of ceramic material as set forth in claim 9 wherein said glass particles are less than ten percent by weight of the gasket material.

11. A body of ceramic material as set forth in claim 9 wherein a layer of pure gold is baked onto the gasket having the glass particles.

12. A body of ceramic material as set forth in claim 9 wherein said gasket is mounted on said surface by baking.

* * * * *